(12) United States Patent
Konwinski et al.

(10) Patent No.: US 8,772,020 B2
(45) Date of Patent: Jul. 8, 2014

(54) FERMENTATION SYSTEM HAVING STRAINER ASSEMBLY

(75) Inventors: Dave Konwinski, Davis, CA (US); Ruihong Zhang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 1109 days.

(21) Appl. No.: 12/375,396

(22) PCT Filed: Aug. 1, 2007

(86) PCT No.: PCT/US2007/075007
§ 371 (c)(1),
(2), (4) Date: Aug. 28, 2009

(87) PCT Pub. No.: WO2008/016999
PCT Pub. Date: Feb. 7, 2008

(65) Prior Publication Data
US 2010/0015679 A1    Jan. 21, 2010

Related U.S. Application Data

(60) Provisional application No. 60/821,095, filed on Aug. 1, 2006.

(51) Int. Cl.
*C12M 3/00* (2006.01)
*C12M 1/00* (2006.01)
*C12M 1/16* (2006.01)
*C12M 1/107* (2006.01)
*C12M 1/26* (2006.01)

(52) U.S. Cl.
CPC ............... *C12M 21/04* (2013.01); *C12M 45/04* (2013.01); *C12M 21/16* (2013.01); *C12M 45/06* (2013.01); *Y02E 50/343* (2013.01); *C12M 33/16* (2013.01)

USPC .................. 435/308.1; 435/299.1; 435/299.2; 435/304.1; 435/289.1; 435/243; 435/261

(58) Field of Classification Search
CPC ...... C12M 45/04; C12M 47/02; C12M 47/10; C12M 47/12; C12M 25/02
See application file for complete search history.

(56) References Cited

U.S. PATENT DOCUMENTS

| | | | | |
|---|---|---|---|---|
| 5,061,366 A | * | 10/1991 | Arai | 210/111 |
| 5,198,111 A | * | 3/1993 | Davis | 210/408 |
| 6,596,521 B1 | * | 7/2003 | Chang et al. | 435/136 |
| 6,634,508 B1 | * | 10/2003 | Ishigaki | 210/415 |

(Continued)

*Primary Examiner* — Nathan Bowers
(74) *Attorney, Agent, or Firm* — Morgan, Lewis & Bockius LLP; Jeffrey S. Mann

(57) ABSTRACT

A fermentation system for production of biogas from solid organic material, the system including at least one fermentation reactor. The fermentation reactor includes a vessel (37) for housing a feed mixture having liquid and solid particles and an outlet port (44), a strainer assembly (33) at the outlet port for filtering processed feed mixture from the vessel, and a biogasification reactor (37) in fluid communication with another fermentation reactor, the other fermentation reactor configured to produce a biomethane. The strainer assembly further includes a mixture driving member (53) positioned in the strainer body (47) adjacent the drain opening (51), the mixture driving member having a driving surface configured to receive the liquid passing through the filter member (60). The driving surface engages the filter member such that solid particles are driven from a surface of the filter member when the driving member is activated. A method of continuously producing a biogas and servicing a strainer assembly for a hydrolysis reactor are disclosed.

26 Claims, 2 Drawing Sheets

(56) References Cited

U.S. PATENT DOCUMENTS

| | | | |
|---|---|---|---|
| 7,767,173 B2* | 8/2010 | Hamano et al. | 422/270 |
| 7,875,448 B2* | 1/2011 | Furey | 435/289.1 |
| 2002/0102673 A1 | 8/2002 | Zhang et al. | |
| 2004/0016525 A1 | 1/2004 | Gervais et al. | |
| 2005/0161391 A1* | 7/2005 | Ettlinger | 210/396 |

* cited by examiner

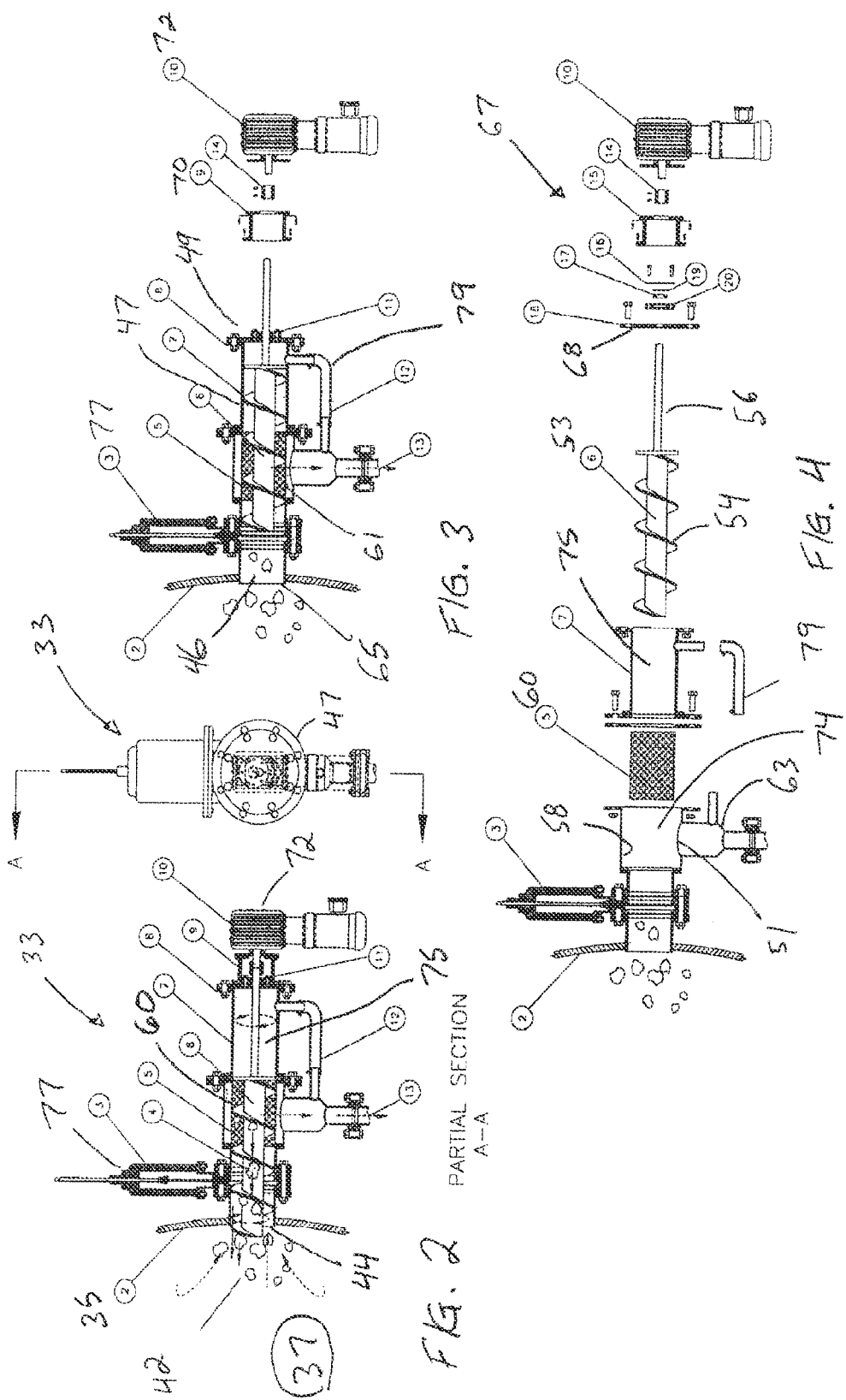

FERMENTATION SYSTEM HAVING STRAINER ASSEMBLY

CROSS-REFERENCES TO RELATED APPLICATIONS

This application claims priority to U.S. Provisional Patent Application No. 60/821,095 filed Aug. 1, 2006, entitled Continuous Self-Cleaning Strainer, the entire content of which is incorporated herein by this reference.

BACKGROUND OF THE INVENTION

This invention relates, in general, to strainers for removing liquid from fermentation reactors and more particularly to strainers for and methods for their use.

An example of such a fermentation system is U.S. Pat. No. 6,342,378, which shows an Anaerobic Phased Solids Digester System (APS-Digester) for producing biogas including hydrogen and methane, and is incorporated herein by reference.

In an APS-Digester System, organic solids are broken down and decomposed in fermentation reactors, such as a hydrolysis reactor, to produce a biogas. A liquid is produced as part of the fermentation reaction. As the process continues, the liquid needs to be removed from the reaction vessel.

In conventional systems, an agitator or pump pushes the liquid into a liquid draining assembly such as a drain hole and drain pipe. The outlet from the vessel is generally located at a lower region of the tank to avoid interfering with the fermentation reaction. With such conventional systems, the mixture pushed into the drain pipe contains liquid-suspended particles and the like which present several operational problems.

Such particulate matter sticks to surfaces and can build up over time. If the solid matter collects above a certain level, it can clog the vessel drain port and drain pipe. Even if a filter is used to prevent the passage of solid material into the drain pipe, the solid matter accumulates on the filter surface. In time, the entire liquid draining assembly must be purged and cleaned. This process requires shutting down the entire reactor which results in significant costs and operational inefficiencies.

Moreover, it is desirable to minimize the loss of the solid particle matter from the vessel through the drain. Particulate solid matter lost through the drain results in decreased efficiency. Because the system digests such matter, a decrease in the amount of solid matter—by expulsion through the drain pipe—leads to lower yields in the fermentation process. Therefore, it is desirable to remove the liquid while retaining any solid matter suspended in the liquid to optimize production of the biogas. The retained solids are preferably put back into the reactor for further decomposition until the particle is too small.

In conventional systems, strainer systems have been employed to address the need to remove liquid from vessels of fermentation reactors, such as anaerobic digesters, while retaining solids. These systems separate liquid from solids being digested in anaerobic digesters and at the same time drain liquid from the digesters. Exemplars of the prior art are strainer systems marketed by Tate Andale Company (Types 105-DS and 1051-DS) and ACME Engineering Products, Inc. (Models ACRS-OF and ACRS-L).

Such conventional strainers allow fluids containing particles to flow into and radially through a vertically oriented cylindrical screen, trapping the particles inside the screen. The trapped particles build-up on the inside surface of the screen and restrict the flow of clear fluids through the screen.

Over time, particles trapped in the strainer restrict the fluid flow out of the reactor vessel. When the flow restriction reaches a pre-determined value, the screen must be cleaned. Cleaning the screen requires shutting off the fluid source. A valve in the bottom of the inside screen cavity is then opened to allow the trapped particles to drop into a catchment container at the bottom of the strainer assembly. An individual then uses a scraper or paddle to sweep and clean the interior of the filter screen dislodging trapped particles that have collected on the inside surface of the screen and dropping them into the bottom catchment container. Once the inside surface of the screen is cleared of particles, the bottom valve is then closed and a drain valve in the lowest end of the bottom catchment container is opened. The operator then flushes fluid through the bottom catchment container (referred to as "blow-down") to remove the collected residue from the system. Closing the bottom valve in the screen chamber and opening the main fluid shut-off valve allows the source fluid to enter once again into the interior of the screen and the filtration process resumes.

This strainer cleaning process periodically repeats with a frequency dependent upon the build-up of flow restriction through the strainer. In other systems, the screen cleaning process is automated by measuring the pressure drop across the filter screen with sensors that send signals to a controller. However, even in an automated system, solid particles trapped in the strainer must be flushed out of the system and therefore do not contribute to biogas production. Further, the cleaning system must still be performed periodically thereby requiring downtime in production.

Conventional strainers and fermentation systems further require periodic cleaning and mixing of the feed mixture in the reactor vessels. Because conventional strainers only provide for moving fluid into the strainer, the reactor vessels are prone to particulate build-up in and around the mouth of the strainer. Such systems also do not provide any means for mixing.

What is needed is a biogas production system and strainer which overcomes the above and other disadvantages of known systems. What is needed is a fermentation system for producing a biogas with decreased particulate build-up and waste. What is needed is an efficient and continuous strainer assembly. What is needed is a strainer assembly for cleaning solid particulate build-up and mixing the feed mixture.

BRIEF SUMMARY OF THE INVENTION

One aspect of the present invention is directed to a fermentation system for production of biogas from solid organic material, the system including at least one fermentation reactor. The fermentation may be a hydrolysis reactor which includes a vessel for housing a feed mixture having liquid and solid particles and an outlet port. The system further includes a strainer assembly at the outlet port for filtering processed feed mixture from the vessel, and a second fermentation reactor in fluid communication with the first fermentation reactor, the second reactor configured to produce a biogas composed of methane. The second fermentation reactor may be biogasification reactor. The strainer assembly includes a strainer body having an inlet end fluidly connected to the vessel, a service end, and a drain opening intermediate the inlet end and service end. The strainer assembly further includes a mixture driving member positioned in the strainer body adjacent the drain opening, the mixture driving member having a driving surface configured to drive solid particles in the strainer body towards the inlet end; a filter member positioned in the drain opening configured to allow liquid effluent to pass therethrough and retain desired solid particles in the strainer body; and a drain pipe configured to receive the liquid passing through the filter member. The driving surface engages the filter member such that solid particles are driven from a surface of the filter member when the driving member is activated.

Another aspect of the present invention is directed to an anaerobic phased digester system including a buffer tank intermediate the hydrolysis reactor and the biogasification reactor. The buffer tank is configured to equilibrate flow from the hydrolysis reactor.

The mixture driving member may be an auger and the driving surface at least one thread. The thread extends from a central axis of the auger to a point adjacent an inner surface of the strainer body. An upstream end of the mixture driving member may extend into the vessel. The filter member surface is substantially flush with an inner surface of the strainer body. The thread of the auger engages the inner surface of the strainer body and filter member surface such that particles are driven from the surfaces. An outer edge of the at least one thread is configured to clean the inner surface of the strainer body and filter member surface. The strainer body is substantially cylindrical and coaxial with the auger. The diameter of the auger is substantially equal to an inner diameter of the strainer body.

The drain opening may be a plurality of openings along a periphery of the strainer body and adjacent the service end. The filter member surface is a cylindrical screen substantially flush with an inner surface of the plurality of drain openings. The filter is configured to retain particles above a predefined threshold within the strainer body. The predefined threshold may be based on dimensions of the solid particles, and the filter member may be a screen having a apertures smaller than a diameter of the smallest solid particles to be retained in the vessel.

Another aspect of the invention is directed to a strainer assembly including a removable end plate assembly at the service end of the strainer assembly configured to seal the service end. The end plate assembly includes an end plate, a motor mount on the end plate configured to mount a rotating shaft of the mixture driving member, and a motor for driving the mixture driving member. The mixture driving member may be removed through the service end of the strainer assembly when the end plate assembly is removed. The mixture driving member may also be moved into a service chamber between the service end and drain opening or out the inlet end of the strainer body. A stop valve positioned adjacent the inlet end of strainer body stops a flow of fluid into the strainer body. The stop valve may be a knife-gate valve.

The mixture driving member is activated when predetermined conditions are met. The mixture driving member may be monolithically formed. The mixture driving member may include a plurality of driving surfaces.

The strainer assembly may be configured to provide hydraulic mixing when the mixture driving member is activated in reversed. The strainer assembly is configured for use with a fermentation reactor housing a liquid with suspended solids.

Another aspect of the invention is directed to a method of continuously producing biogas. The method includes the steps of proving a feed mixture, feeding the mixture to a fermentation reactor configured to produce a biogas comprising hydrogen, allowing the mixture to react in the reactor, collecting a biogas, transferring the reacted feed mixture composed of liquid and liquid-suspended particles from the fermentation reactor to the strainer assembly, driving the mixture driving member when predetermined conditions are met, and receiving liquid passing through the strainer into a drain pipe while retaining solids. A plurality of supplementary hydrolysis reactors may be provided such that the liquid is fed back into the first hydrolysis reactor or to any of the supplementary reactors. The liquid may subsequently run through the supplementary reactors in parallel or in series. A biogasification reactor may be provided to receive the collected liquid and produce a biogas including methane.

Yet another aspect of the invention is directed to a method of servicing a hydrolysis reactor vessel and strainer assembly including the steps of providing a strainer assembly as above, driving the mixture driving member under operating conditions, removing the end cap assembly during service conditions, and moving the mixture driving member out of the operating chamber.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIG. 2 is a side view of a strainer assembly and a cross-sectional view of the strainer assembly taken through the line A-A, the strainer assembly shown in accordance with various aspects of the present invention.

FIG. 3 is an exploded cross-sectional view of the strainer assembly of FIG. 2 illustrating removal of the motor mount and motor.

FIG. 4 is an exploded cross-sectional view of the strainer assembly of FIG. 2.

DETAILED DESCRIPTION OF THE INVENTION

Figure 1:
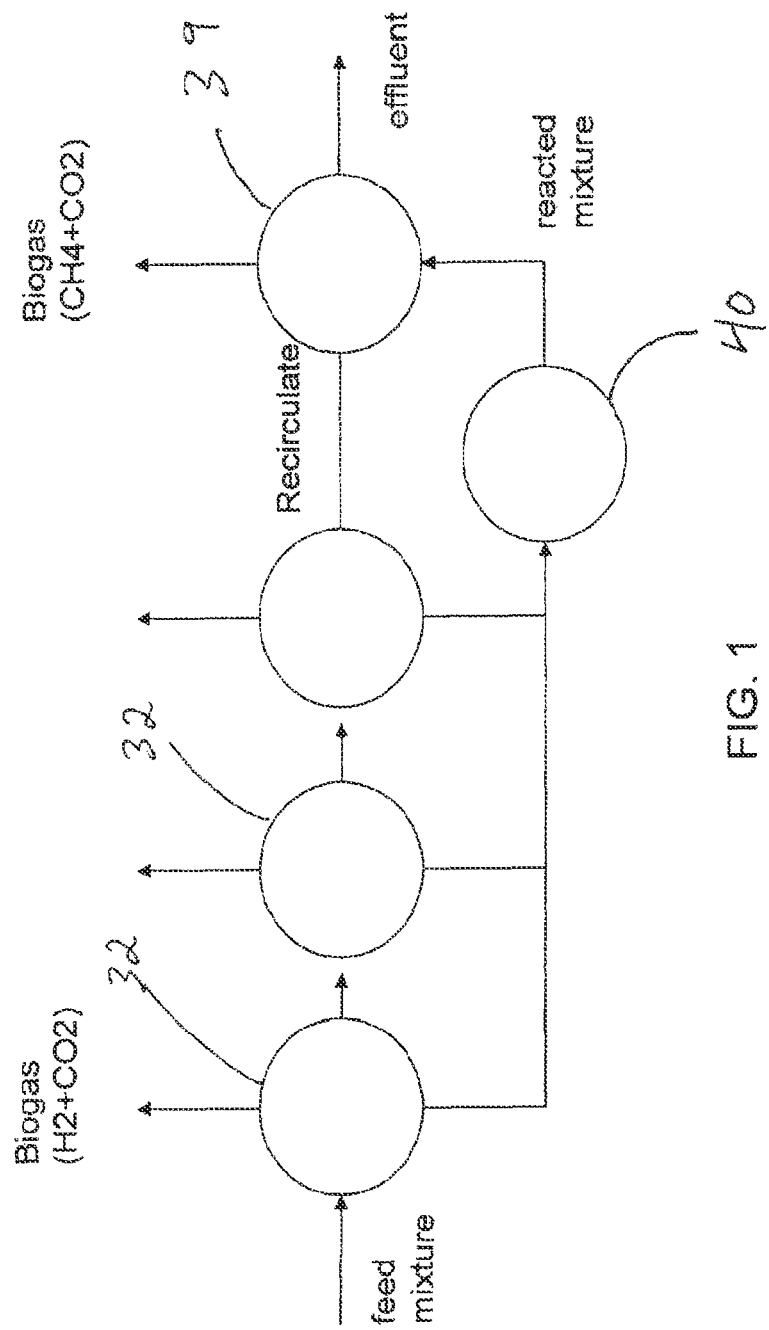
FIG. 1 a schematic view of a fermentation system in accordance with the present invention.

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Turning now to the drawings, wherein like components are designated by like reference numerals throughout the various figures, attention is directed to FIGS. 1-3. In the exemplary embodiment shown in FIG. 1, a fermentation system, generally designated 30, is shown with fermentation reactor 32. A strainer assembly, generally designated 33, is attached to a side wall 35 of a vessel 37 of the fermentation reactor.

In the illustrated embodiment, the fermentation reactor is a hydrolysis reactor producing a biogas including hydrogen and carbon dioxide. The hydrolysis reactor is part of an anaerobic phased solids digester system such as the ones disclosed in our Letters Patent, U.S. Pat. No. 6,342,378 and International Patent Application No. PCT/US2006/048564 filed Dec. 18, 2006, the entire contents of which are incorporated herein by this reference. The system further includes a biogasification reactor 39 for producing a biogas including methane and carbon dioxide from a liquid mixture from the hydrolysis reactor. The biogasification reactor is fluidly connected to the hydrolysis reactor via a buffer tank 40. The buffer tank is fluidly positioned intermediate the hydrolysis reactor and the biogasification reactor. The buffer tank is configured to equilibrate flow from the hydrolysis reactor. For example, the physical and chemical properties of the mixture, including but not limited to pH level and temperature, may be adjusted to desired levels in the buffer tank before passing to subsequent reactor vessels.

Suitable materials for use as feed mixture in the fermentation system include, but are not limited to, various organic materials and process wastewater. The wastewater may contain any percentage of solid content. In one embodiment, the solids content is less than 5% or more than 40%. In the illustrated embodiment, the fermentation reactor is configured to handle any organic material in almost any solids content form. In the illustrated embodiment, the liquid effluent from the hydrolysis reactor contains organic acids produced in the reactor and used as feed for the biogasification reactor. In one embodiment, the mixture driving member is used to control the amount of suspended solids introduced to the biogasification reactor. In one embodiment, build-up of solids in the biogasification reactor is reduced by mixing or cleaning using a strainer assembly in accordance with the present invention.

A feed mixture containing solid organic material 42 is housed within the reactor vessel 37. The mixture flows through an outlet port 44 in the vessel wall 35 and into strainer assembly 33. The liquid mixture flowing into the strainer assembly includes liquid and solid particles.

Strainer assembly 33 is positioned at the outlet port for filtering the feed mixture after it is processed in hydrolysis reactor 32 and before it is fed to another reactor. In this manner, an inlet end 46 of the strainer assembly is fluidly connected to the vessel. Strainer assembly 33 includes a strainer body or housing 47 having inlet end 46 facing the reactor vessel and a service end 49 at an opposite end of the body. A drain opening 51 is positioned intermediate the inlet end and service end.

A mixture driving member 53 is positioned in the strainer body adjacent drain opening 51. The mixture driving member has a driving surface 54 configured to drive solid particles in the strainer body towards the inlet end. In the illustrated embodiment, the mixture driving member is an auger having a central axis 56 and thread acting as a driving surface 54. The auger may be monolithically formed with the thread extending from the central axis to a point adjacent an inner surface of the strainer body 58. The auger is mounted in a horizontal fashion with one end extending beyond inlet end 46 of the strainer body into reactor vessel 37.

The mixture driving member may also have other driving surface configurations. In one embodiment, the mixture driving member includes a plurality of driving surfaces. In one embodiment, the mixture driving member includes a variety of driving surfaces to perform different functions like breaking up solids, sweeping surfaces, and the like, together or separately. Other configurations are envisioned within the scope of the invention including, but not limited to a plurality of screws, propellers, and like fluid moving and cleaning assemblies.

In one embodiment, the thread extends all the way to the inner surface. Therefore, as the auger rotates, the thread catches solid particles in the strainer body and along the strainer body surface. The operational direction of the auger is such that when it rotates the solid particles are pushed back to inlet end 46. In the illustrated embodiment, an upstream end of the auger extends a short distance past the inlet end into the vessel 37. This allows a tip of the auger to break-up any potential blockages of solid materials that might occur against the side walls of the vessel. This further allows liquid to flow into the strainer body while retaining solid materials in the vessel.

Strainer assembly 33 includes a filter member 60 positioned in drain opening 51. The filter member is configured to allow liquid effluent to pass through and into the drain opening while retaining desired solid particles in the strainer body. In the illustrated embodiment, the filter member is a cylindrical screen formed along the periphery of the strainer body. Other filter member configurations are envisioned including, but not limited to, a trap and screen configuration, an absorbent or adsorbent material, and the like. The filter member may be formed of multiple pieces or monolithically formed.

The driving surface of mixture driving member 53 is configured to engage the filter member such that solid particles are driven from a surface of the filter member when the driving member is activated. In the illustrated embodiment, a surface 61 of filter member 60 is substantially flush with inner surface 58 of the strainer body. In this manner, thread 54 engages inner surface 58 of the strainer body and filter member surface 61 such that particles adhering to one or both surfaces are driven from the surfaces.

In the one embodiment, an outer edge of the auger thread is further configured to clean the inner surface of the strainer body and filter member surface. For example, the edge of the thread may be configured to facilitate breaking up of particles on the surface or scraping of the surface with a sharp edge.

In the illustrated embodiment, strainer body 47 is substantially cylindrical and coaxial with auger 53. The diameter of the auger is substantially equal to an inner diameter of the strainer body such that the outer edge of the auger extends to the inner surface of the strainer body. Other configurations and shapes are envisioned to push solid particles back into the vessel and further cleaning of the inner surfaces of the strainer body and filter member. In the illustrated strainer assembly, the orientation of the strainer screen and body are horizontal; however, other orientations and configurations are within the scope of the invention.

Drain opening 51 is configured to receive fluid passing through the filter member. The drain opening is located at an intermediate position between inlet end 46 and opposite service end 49 of the strainer body. A drain pipe fitting is installed in the strainer body to fasten a drain pipe 63 and allow the liquid to flow out of the strainer body and into a liquid collection system.

In the illustrated embodiment, the drain opening is a plurality of openings or a gap along a periphery of the strainer body adjacent and prior to service end 49. In one embodiment, filter member 60 is a cylindrical screen substantially flush with an inner surface of the drain opening. In one embodiment, filter member 60 includes a filter with the cylindrical screen positioned between the filter and inner cavity of the strainer body. The illustrated filter is configured to retain particles above a predefined threshold within the strainer body. The predefined threshold may be based on dimensions of the solid particles such that the openings in the filter screen are smaller than the smallest solid particle to be allowed into the drain opening.

In one embodiment, the clearance between auger thread 54 and filter screen 60 will be a minimal distance. This allows the auger rotation to keep the screen clear of solids and assist in keeping the screen unplugged thereby self-cleaning the strainer assembly and allowing maximum water flow. The screen sizing and screen surface area may be determined by the size of solids that need to be retained in the reactor and the liquid flow rate required. Other screen and filter member configurations may be suitable depending on the application. In one embodiment, the strainer assembly optionally includes a strainer screen 65 positioned at the mouth of the strainer body to further protect against solid particles flowing out of the vessel and potentially into the drain pipe. The liquid effluent to be removed from the reactor through the strainer assembly will be a high liquid stream with suspended solids below a predetermined particle size. The size may vary based on the type of organic materials loaded into the reactor and the circulation requirements.

In the illustrated embodiment, the strainer assembly includes a removable end plate assembly, generally designated 67 at the service end of the strainer assembly. The end plate assembly is configured to seal service end 49 by an o-ring or other known sealing means. The end plate assembly includes an end plate 68 and motor mount 70 on the end plate configured to mount a rotating shaft of the mixture driving member. The motor mount fits onto the end plate and includes a central aperture for receiving a shaft of the auger. The end plate assembly includes a motor 72 for driving mixture driving member 53.

The end plate assembly allows for simple maintenance. In the illustrated embodiment, the auger and inside of the strainer body may be accessed by removing the end plate and removing the mixture driving member through the service end of the strainer assembly.

The method of producing a biogas using a fermentation system in accordance with the present invention can now be described. The illustrated fermentation system includes a hydrolysis reactor and biogasification reactor; however, the fermentation system may include a plurality of such reactors in accordance with the present invention.

In the illustrated embodiment, fermentation system 30 is an anaerobic phased solids digester system and fermentation reactor 32 is a hydrolysis reactor. As discussed above, a plurality of supplementary hydrolysis reactors may be provided such that the liquid effluent is passed from one hydrolysis reactor to another for further refinement and biogas production. The reactors may also be positioned in parallel or in other configurations depending on the application. The liquid effluent may also be fed back into the same hydrolysis reactor. As the feed mixture reacts in each reactor and passes from hydrolysis reactor 32 to biogasification reactor 39, a biogas is produced. The hydrolysis reactor is configured to produce a biogas including hydrogen. The biogasification reactor is configured to produce a biogas including methane. The biogas is collected continuously as the feed mixture flows through the system.

Feed mixture is first fed to the fermentation reactors. As the feed mixture reacts inside the reactor vessel 37, mixture is transferred from the fermentation reactor to strainer assembly 33. In an APS-Digester System, part of the liquid in hydrolysis reactors 32 needs to be removed on continuous or intermittent basis. The liquid contains water-soluble compounds and fine particulate matter, most of which are generated as organic solids are broken down and decomposed in the reactors due to hydrolytic and biochemical reactions. After the liquid is removed from the hydrolysis reactors, it is collected and transferred to another reactor, the biogasification reactor. The mixture driving member may also be activated in reverse to pump the liquid back into the same hydrolysis reactor to provide hydraulic mixing. As the liquid is removed from each hydrolysis reactor, solids 42 of predetermined particle size (e.g. >1 mm) need to be retained in the reactor to undergo further decomposition. As will be described below, in operation the strainer assembly in accordance with the present invention allows the liquid removal and transferring as required by the engineering design of an APS-Digester system. The mechanical device would normally be installed on a side of a vessel at one or more levels.

A feed mixture is first fed into fermentation reactor 32. The reactor is configured to produce a biogas comprising hydrogen from the feed mixture, for example, as described in our U.S. Pat. No. 6,342,378. The mixture is allowed to react in the hydrolysis reactor. As the biogas is given off, it is collected from the reactor.

After the mixture solution passes through the strainer assembly it is received in drain pipe 63. The liquid effluent is then collected in a liquid collection vessel (not shown) and transferred elsewhere.

Fluids containing suspended particles 42 flow directly into a center of the strainer screen 60 past the continuously rotating thread surfaces 54 of the self-cleaning mixture driving member. The auger driving surfaces 54 not only scrape and clean the filter surface but also continuously push suspended particles in the liquid back upstream. In this manner, suspended particles in the liquid are not allowed to pack-up on the inside surface of the filter, which would restrict liquid flow through the system.

In operation and use, the mixture driving member is activated when predetermined conditions are met. In the application of removing liquid from the hydrolysis reactors in the APS-Digester system, the continuous self-cleaning strainer will support the operation of several processes as described below. In one embodiment, a valve is installed on drain pipe 63 that extends from the strainer body into the liquid collection system to regulate liquid to flow. The continuous self-cleaning strainer assembly can be used to remove the liquid from reactor vessel 37 with mixture driving member 53 either activated or not activated, depending on the requirement of operation, such as in an anaerobic digestion system. When the mixture driving member is activated, the strainer assembly allows liquid to flow out of the reactor vessel with the mixture driving member actively pushing the solids back into the vessel. When the mixture driving member is deactivated, the mixture driving member still allows the liquid to flow out of tank by force of gravity.

As mentioned above, several operations are supported by the strainer assembly in the illustrated embodiment. In particular, the strainer assembly allows for decanting and mixing operations in a hydrolysis reactor. A control system (not shown) provides for control and activation of the mixture driving member in the strainer assembly.

The decanting process of the hydrolysis reactor will first be described. In the decanting process, the mixture driving member is not activated. Therefore, liquid flows passively by the force of gravity from vessel 37 into strainer assembly 33 and into the liquid collection system. This operation passively decants the hydrolysis reactor. The mixture driving member, in the illustrated case an auger, will not be in operation during the "decant" process.

In the illustrated embodiment, the control system will determine the time required for a set number of gallons of water to be removed from the reactor. If the liquid flow rate is too small for the pre-set flow rate, the computer control will activate the strainer system for a short time period to clear the strainer body and restore the liquid flow.

The strainer assembly in the illustrated embodiment further allows for mixing of the hydrolysis reactor. In the mixing operation, the strainer assembly allows liquid to flow out of the strainer assembly with mixture driving member 53 activated and turning inward. In this manner, fluid is pushed upstream keeping strainer body 47 clear of solids. The speed of the auger will be determined by the flow rate required for the mixing process.

In the illustrated embodiment, as fluid enters strainer assembly 33, it passes threads 54 carrying large particles in the flow. To preclude particles from packing up and clogging screen 65 of the filter member, the thread is made to rotate clockwise by a speed-reduced motor. The solid particles are swept away from the internal surface of the filter screen by the threads and are moved upstream in the liquid flow, back into the container. The auger continuously rotates during liquid flow thereby cleaning the screen and moving the solids back into the vessel. The mixture driving member type and configuration may vary depending on the application in accordance with the present invention.

On occasion, users may require access to the mixture driving member and inner cavity of the strainer assembly for maintenance. Turning now to FIGS. 1-4, the maintenance operation can now be described. The strainer assembly in accordance with the present invention provides for simple disassembly and maintenance during service conditions. In one embodiment, the mixture driving member may be moved from an operating chamber 74 adjacent the inlet end as shown in FIG. 1 to a service chamber 75 downstream from drain opening 51.

To allow removal of strainer assembly 33 from vessel 37 without draining the vessel, a shut-off valve 77 closes the flow of liquid from the vessel into the strainer body. The shut-off valve is mounted directly to the vessel and the strainer assembly is mounted to the opposite side of the valve. In the illustrated embodiment, the shut-off valve is a knife-gate valve positioned adjacent the inlet end of the strainer body between strainer body 47 and vessel wall 35. Other configurations are envisioned including, but not limited to, a true gate, ball valve, or plug valve.

To remove the mixture driving member, the valve in the liquid drain pipe 63 is closed. Once the flow is shut off, the mixture driving member may be removed. End cap assembly 67 is removed such that the mixture driving member may slide out of the service end of the strainer body. In the illustrated embodiment, a shaft seal for the auger shaft is provided to maintain a seal of the service chamber. The seal further allows for pressure to equalize through the drain pipe into a drain tube 79 connecting the drain pipe to the service chamber adjacent the service end. Drive motor 72, a gear reducer and a flexible coupling housing are disconnected from the main system or strainer body. The mixture driving member is then pulled away from the strainer body. In one embodiment, the mixture driving member is pulled through the inlet end until it clears shut-off valve 77. In one embodiment, the mixture driving member is pulled into service chamber 75 and optionally out of the strainer body through service end 49. To preclude liquid from flowing out of the vessel, the illustrated embodiment includes an internal barrier seal that remains in the main strainer body until the shut-off valve is fully closed. The mixture driving member, barrier seal, flexible coupling, and motor mounting flange are then fully extracted for servicing. To re-install the strainer body assembly, the disassembly process is reversed.

The fermentation system and strainer assembly of the present invention have several advantages over conventional systems. As described above, the strainer assembly is self-cleaning whereby the mixture driving member can clean the inner surfaces of strainer body 47 and filter member 60. The strainer assembly of the present invention further allows for the fermentation system to be operated continuously. During the decanting process, liquid flows through the strainer assembly and into the liquid collection system. As necessary, the strainer assembly cleans itself and purges solid particles trapped inside the assembly. The strainer assembly and fermentation system of the present invention therefore provide for reduces downtime and increased efficiency. The strainer assembly of the present invention further provides for several additional features such as mixing and the like.

For convenience in explanation and accurate definition in the appended claims, the terms "up" or "upper", "down" or "lower", "inside" and "outside" are used to describe features of the exemplary embodiments with reference to the positions of such features as displayed in the figures.

In many respects various modified features of the various figures resemble those of preceding features and the same reference numerals followed by subscripts "a", "b", "c", and "d" designate corresponding parts.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A fermentation system for production of biogas from solid organic material, said system comprising:
    a first fermentation reactor configured to produce a first biogas including:
        a vessel for housing a feed mixture having liquid and solid particles, the vessel containing an outlet port;
        a strainer assembly at the outlet port for filtering processed feed mixture from the vessel, the strainer assembly including:
            a strainer body having an inlet end fluidly connected to the vessel, service end, and drain opening intermediate the inlet end and service end;
            a mixture driving member positioned in the strainer body adjacent the drain opening, the mixture driving member having a driving surface configured to drive solid particles in the strainer body towards the inlet end and an upstream end configured to extend beyond the inlet end into the vessel;
            a filter member positioned in the drain opening configured to allow liquid effluent to pass therethrough and retain desired solid particles in the strainer body; and
            a drain pipe configured to receive the liquid passing through the filter member; and
    a second fermentation reactor in fluid communication with the first reactor, the second reactor configured to produce a second biogas,
    wherein the driving surface engages the filter member such that solid particles are driven from a surface of the filter member when the driving member is activated.

2. The system according to claim 1, wherein the fermentation system is an anaerobic phased digester system, wherein the first fermentation reactor is a hydrolysis reactor and the second fermentation reactor is a biogasification reactor, the system further including:

a buffer tank intermediate the hydrolysis reactor and the biogasification reactor, wherein the buffer tank is configured to equilibrate flow from the hydrolysis reactor.

3. The system according to claim 2, wherein strainer assembly is configured to regulate the flow of suspended solids introduced to the biogasification reactor.

4. The system according to claim 1, wherein the mixture driving member is an auger and the driving surface is at least one thread, the at least one thread extending from a central axis of the auger to a point adjacent an inner surface of the strainer body.

5. The system according to claim 4, wherein the filter member surface is substantially flush with an inner surface of the strainer body.

6. The system according to claim 5, wherein the at least one thread engages the inner surface of the strainer body and filter member surface such that particles are driven from the surfaces.

7. The system according to claim 6, wherein an outer edge of the at least one thread is configured to clean the inner surface of the strainer body and filter member surface.

8. The system according to claim 5, wherein the strainer body is substantially cylindrical and coaxial with the auger, a diameter of the auger is substantially equal to an inner diameter of the strainer body.

9. The system according to claim 8, wherein the drain opening is a plurality of openings along a periphery of the strainer body and adjacent the service end and the filter member surface is a cylindrical screen substantially flush with an inner surface of the plurality of drain openings.

10. The system according to claim 1, wherein the filter is configured to retain particles above a predefined threshold within the strainer body.

11. The system according to claim 10, wherein the predefined threshold is based on dimensions of the solid particles.

12. The system according to claim 1, further including a removable end plate assembly at the service end of the strainer assembly configured to seal the service end, the end plate assembly including:
 an end plate;
 a motor mount on the end plate configured to mount a rotating shaft of the mixture driving member; and
 a motor for driving the mixture driving member,
 wherein the mixture driving member may be removed through the service end of the strainer assembly when the end plate assembly is removed.

13. The system according to claim 1, wherein the mixture driving member is activated when predetermined conditions are met.

14. The system according to claim 1, wherein the mixture driving member is monolithically formed.

15. The system according to claim 1, wherein the mixture driving member includes a plurality of driving surfaces.

16. The system according to claim 1, wherein strainer assembly is configured to provide hydraulic mixing when the mixture driving member is activated in reversed.

17. The strainer assembly according to claim 1, wherein the filter member is a screen having a plurality of apertures, the apertures being smaller than a diameter of the smallest solid particles to be retained in the vessel.

18. The strainer assembly according to claim 1, further including a shut-off valve adjacent the inlet end of the strainer body configured to stop a flow of mixture into the strainer body.

19. A method of continuously producing biogas using the fermentation system according to claim 1, the method comprising the steps of:
 providing the feed mixture;
 feeding the feed mixture to the first fermentation reactor configured to produce the biogas from the feed mixture;
 reacting the feed mixture in a hydrolysis reactor;
 transferring reacted feed mixture composed of liquid and liquid-suspended particles from the hydrolysis reactor to the strainer assembly configured to strain liquid from the reacted mixture;
 driving the mixture driving member when predetermined conditions are met;
 receiving the liquid passing through the strainer assembly into the drain pipe; and
 collecting biogas from the first fermentation reactor.

20. The method according to claim 19, further including the steps of:
 providing a plurality of supplementary fermentation reactors,
 wherein the collected liquid is fed to one of the second fermentation reactor or supplementary fermentation reactors.

21. The method according to claim 20, wherein the first fermentation reactor and supplementary fermentation reactors are hydrolysis reactors, further including the steps of:
 providing a biogasification reactor for producing a biogas comprising methane;
 feeding the collected liquid from the drain pipe to one of the hydrolysis reactor, supplementary hydrolysis reactors, or biogasification reactor; and
 collecting biogas from at least one of the hydrolysis reactor, supplementary hydrolysis reactors, or biogasification reactor.

22. The method according to claim 21, wherein the mixture driving member is an auger and the driving surface is at least one thread, the at least one thread extending from a central axis of the auger to a point adjacent an inner surface of the strainer body, further wherein the at least one thread engages a surface of the filter member such that particles are driven from the surface of the filter.

23. The method according to claim 22, wherein the strainer body is substantially cylindrical and coaxial with the mixture driving member, the mixture driving member and an inner surface of the strainer body being substantially equal in diameter.

24. The method according to claim 23, wherein the drain opening is a plurality of openings along a periphery of the strainer body and the filter member is a cylindrical screen.

25. The method according to claim 22, further including the steps of:
 providing a removable end cap assembly configured to seal the service end of the strainer body, a portion of the strainer body between the drain opening and the end cap defining a service chamber, the end cap assembly being configured to mount the central axis of the mixture driving member;
 stopping a flow of the mixture into the strainer body to the drain opening;
 removing the end cap assembly; and
 moving the mixture driving member out of the strainer body past one end of the strainer body.

26. The method according to claim 25, wherein the stopping step is performed by a shut-off valve positioned adjacent the inlet end of the strainer body.

* * * * *